(12) United States Patent
Flaherty et al.

(10) Patent No.: US 6,830,558 B2
(45) Date of Patent: Dec. 14, 2004

(54) FLOW CONDITION SENSOR ASSEMBLY FOR PATIENT INFUSION DEVICE

(75) Inventors: J. Christopher Flaherty, Topsfield, MA (US); Christopher C. Gregory, Newton, PA (US); Sterling Eduard McBridge, Princeton, NJ (US); Richard Morgan Moroney, III, Princeton, NJ (US)

(73) Assignee: Insulet Corporation, Bedford, NH (US)

( * ) Notice: Subject to any disclaimer, the term of this patent is extended or adjusted under 35 U.S.C. 154(b) by 453 days.

(21) Appl. No.: 10/086,344

(22) Filed: Mar. 1, 2002

(65) Prior Publication Data

US 2003/0167035 A1 Sep. 4, 2003

(51) Int. Cl.[7] .................. A61M 31/00; A61M 1/00
(52) U.S. Cl. ........................... 604/67; 604/31
(58) Field of Search ................ 604/67, 118, 131, 604/151–153, 30, 31, 167.01, 167.03; 417/12, 38

(56) References Cited

U.S. PATENT DOCUMENTS

| 3,631,847 A | 1/1972 | Hobbs |
| 3,812,843 A | 5/1974 | Wootten et al. |

(List continued on next page.)

FOREIGN PATENT DOCUMENTS

| DE | 4200595 | 7/1993 |
| DE | 19920896 | 9/2000 |
| EP | 0342947 | 5/1989 |
| EP | 0763369 | 3/1997 |
| EP | 0867196 | 3/1998 |
| EP | 0937475 | 8/1999 |
| WO | WO81/01658 | 6/1981 |
| WO | WO86/06796 | 11/1986 |
| WO | WO98/00193 | 1/1998 |
| WO | WO98/01071 | 1/1998 |
| WO | WO99/10040 | 3/1999 |
| WO | WO00/19887 | 9/1999 |
| WO | WO99/62576 | 9/1999 |
| WO | WO99/56803 | 11/1999 |
| WO | WO0010628 | 3/2000 |
| WO | WO00/29047 | 5/2000 |
| WO | WO00/29049 | 5/2000 |
| WO | WO00/74752 | 5/2000 |
| WO | WO00/30705 | 6/2000 |
| WO | WO00/78210 | 6/2000 |

(List continued on next page.)

OTHER PUBLICATIONS

US 5,954,699, 9/1999, Jost et al. (withdrawn)
Web–Site Brochure dated Jan. 4, 2000. MiniMed 508. "Doing its job. Naturally." www.minimed.com/tiles/mn_113.htm.

(List continued on next page.)

*Primary Examiner*—Sharon Kennedy (57) ABSTRACT

A device for delivering fluid to a patient including an exit port assembly adapted to connect to a transcutaneous patient access tool, a flow path extending from the exit port assembly, and a flow condition sensor assembly. The sensor assembly includes a resilient diaphragm having a first surface positioned against the flow path, a chamber wall defining a sensor chamber adjacent a second surface of the diaphragm, and at least one sensor arranged to provide a threshold signal when the second surface of the diaphragm expands into the chamber in response to at least one predetermined fluid flow condition occurring in the flow path. The sensor includes a first electrode secured on the diaphragm, a second electrode positioned in a fixed location with respect to the first electrode, and an impedance meter connected between the electrodes.

86 Claims, 5 Drawing Sheets

U.S. PATENT DOCUMENTS

| | | |
|---|---|---|
| 4,067,000 A | 1/1978 | Carlson |
| 4,108,177 A | 8/1978 | Pistor |
| 4,151,845 A | 5/1979 | Clemens |
| 4,193,397 A | 3/1980 | Tucker et al. |
| 4,211,998 A | 7/1980 | Junginger et al. |
| 4,231,019 A | 10/1980 | Junginger et al. |
| 4,268,150 A | 5/1981 | Chen |
| 4,364,385 A | 12/1982 | Lossef |
| 4,373,527 A | 2/1983 | Fischell |
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A | 3/1985 | Kambara et al. |
| 4,514,732 A | 4/1985 | Hayes, Jr. |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,560,979 A | 12/1985 | Rosskopk |
| 4,562,751 A | 1/1986 | Nason et al. |
| 4,585,439 A | 4/1986 | Michel |
| 4,601,707 A | 7/1986 | Albisser et al. |
| 4,624,661 A | 11/1986 | Arimond |
| 4,634,427 A | 1/1987 | Hannula et al. |
| 4,678,408 A | 7/1987 | Nason et al. |
| 4,684,368 A | 8/1987 | Kenyon |
| 4,685,903 A | 8/1987 | Cable et al. |
| 4,734,092 A | 3/1988 | Millerd |
| 4,755,173 A | 7/1988 | Konopka et al. |
| 4,781,688 A | 11/1988 | Thoma et al. |
| 4,781,693 A | 11/1988 | Martinez et al. |
| 4,801,957 A | 1/1989 | Vandemoere |
| 4,808,161 A | 2/1989 | Kamen |
| 4,836,752 A | 6/1989 | Burkett |
| D303,013 S | 8/1989 | Konopka |
| 4,855,746 A | 8/1989 | Stacy |
| 4,871,351 A | 10/1989 | Feingold |
| 4,882,600 A | 11/1989 | Van de Moere |
| 4,886,499 A | 12/1989 | Cirelli et al. |
| 4,898,579 A | 2/1990 | Groshong et al. |
| D306,691 S | 3/1990 | Arai |
| 4,944,659 A * | 7/1990 | Labbe et al. |
| D311,735 S | 10/1990 | Aran et al. |
| 4,969,874 A | 11/1990 | Michel et al. |
| 4,973,998 A | 11/1990 | Gates |
| D315,727 S | 3/1991 | Arai et al. |
| 5,007,458 A | 4/1991 | Marcus et al. |
| 5,045,871 A | 9/1991 | Reinholdson |
| 5,062,841 A | 11/1991 | Siegel |
| 5,109,850 A | 5/1992 | Blanco et al. |
| 5,176,662 A | 1/1993 | Bartholomew et al. |
| 5,178,609 A | 1/1993 | Ishikawa |
| 5,205,819 A | 4/1993 | Ross et al. |
| 5,213,483 A | 5/1993 | Flaherty et al. |
| 5,232,439 A | 8/1993 | Campbell et al. |
| 5,239,326 A | 8/1993 | Takai |
| 5,242,406 A | 9/1993 | Gross et al. |
| 5,244,463 A | 9/1993 | Cordner, Jr. et al. |
| 5,254,096 A | 10/1993 | Rondelet et al. |
| 5,257,980 A | 11/1993 | Van Antwerp et al. |
| 5,281,202 A | 1/1994 | Weber et al. |
| 5,308,335 A | 5/1994 | Ross et al. |
| 5,312,337 A | 5/1994 | Flaherty et al. |
| 5,318,540 A | 6/1994 | Athayde et al. |
| 5,342,313 A | 8/1994 | Campbell et al. |
| 5,346,476 A * | 9/1994 | Elson |
| 5,364,342 A | 11/1994 | Beuchat et al. |
| 5,411,480 A | 5/1995 | Kriesel |
| 5,433,710 A | 7/1995 | Van Antwerp et al. |
| 5,452,033 A | 9/1995 | Balling et al. |
| 5,492,534 A | 2/1996 | Athayde et al. |
| 5,505,709 A | 4/1996 | Funderburk et al. |
| 5,507,288 A | 4/1996 | Bocker et al. ............... 128/633 |
| 5,514,096 A | 5/1996 | Hiejima |
| 5,533,389 A | 7/1996 | Kamen et al. |
| 5,545,152 A | 8/1996 | Funderburk et al. |
| 5,575,770 A | 11/1996 | Melsky et al. |
| 5,576,781 A | 11/1996 | Deleeuw |
| 5,582,593 A | 12/1996 | Hultman |
| 5,584,813 A | 12/1996 | Livingston et al. |
| 5,630,710 A | 5/1997 | Tune et al. |
| 5,637,095 A | 6/1997 | Nason et al. |
| 5,643,213 A | 7/1997 | McPhee |
| 5,647,853 A | 7/1997 | Feldmann et al. |
| 5,660,728 A | 8/1997 | Saaski et al. |
| 5,665,065 A | 9/1997 | Colman et al. |
| 5,665,070 A | 9/1997 | McPhee |
| 5,695,490 A | 12/1997 | Flaherty et al. |
| 5,702,363 A | 12/1997 | Flaherty |
| 5,704,520 A | 1/1998 | Gross |
| 5,726,404 A | 3/1998 | Brody |
| 5,726,751 A | 3/1998 | Altendorf et al. |
| 5,741,228 A | 4/1998 | Lambrecht et al. |
| 5,747,350 A | 5/1998 | Sattler |
| 5,748,827 A | 5/1998 | Holl et al. |
| 5,755,682 A | 5/1998 | Knudson et al. |
| 5,776,103 A | 7/1998 | Kriesel et al. |
| 5,779,676 A | 7/1998 | Kriesel et al. |
| 5,785,681 A | 7/1998 | Indravudh |
| 5,785,688 A | 7/1998 | Joshi et al. |
| 5,797,881 A | 8/1998 | Gadot |
| 5,800,397 A | 9/1998 | Wilson et al. |
| 5,800,405 A | 9/1998 | McPhee |
| 5,810,015 A | 9/1998 | Flaherty |
| 5,814,020 A | 9/1998 | Gross |
| 5,839,467 A | 11/1998 | Saaski et al. |
| 5,840,063 A | 11/1998 | Flaherty |
| 5,845,218 A | 12/1998 | Altschul |
| 5,848,991 A | 12/1998 | Gross et al. |
| 5,851,197 A | 12/1998 | Marano et al. |
| 5,858,005 A | 1/1999 | Kriesel |
| D405,524 S | 2/1999 | Falk et al. |
| 5,875,393 A | 2/1999 | Altschul et al. |
| 5,886,647 A | 3/1999 | Badger et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,931,814 A | 8/1999 | Alex et al. |
| 5,935,099 A | 8/1999 | Peterson et al. |
| 5,954,058 A | 9/1999 | Flaherty |
| 5,957,890 A | 9/1999 | Mann et al. |
| 5,961,492 A | 10/1999 | Kriesel et al. |
| 5,965,848 A | 10/1999 | Altschul et al. |
| 5,983,094 A | 11/1999 | Altschul et al. |
| 5,993,423 A | 11/1999 | Choi |
| 5,997,501 A | 12/1999 | Gross et al. |
| 6,019,747 A | 2/2000 | McPhee |
| 6,024,539 A | 2/2000 | Blomquist |
| 6,061,580 A | 5/2000 | Altschul et al. |
| 6,071,292 A | 6/2000 | Makower et al. |
| 6,144,847 A | 11/2000 | Altschul et al. |
| 6,152,898 A | 11/2000 | Olsen |
| 6,174,300 B1 | 1/2001 | Kriesel et al. |
| 6,190,359 B1 | 2/2001 | Heruth |
| 6,206,850 B1 | 3/2001 | O'Neil |
| 6,375,638 B2 | 4/2002 | Nason et al. |
| 6,520,936 B1 * | 2/2003 | Mann |
| 6,527,744 B1 | 3/2003 | Kriesel et al. |

| | | | |
|---|---|---|---|
| 6,692,457 B2 * | 2/2004 | Flaherty | 604/67 |
| 2004/0068224 A1 * | 4/2004 | Couvillon et al. | 604/67 |

FOREIGN PATENT DOCUMENTS

| WO | WO00/48112 | 8/2000 |
|---|---|---|
| WO | WO00/61215 | 10/2000 |
| WO | WO01/52727 | 1/2001 |
| WO | WO01/5663 | 8/2001 |
| WO | WO01/76684 | 10/2001 |
| WO | WO 02/20073 | 3/2002 |
| WO | WO02/26282 | 4/2002 |

OTHER PUBLICATIONS

Web–Site Brochure dated Dec. 20, 1999. Applied Medical Technology. "508 Pump Information". www.applied-medical.co.uk/508.htm.

Web–Site Brochure dated Jan. 4, 2000. "The Glucose Sensor". www.animascorp.com/sensor_f.html.

Web–Site Brochure dated Dec. 20, 1999. "The Animas R–1000 Insulin Pump". www.animascorp.com/pump_f_s.html.

Web–Site Brochure dated Dec. 20, 1999. "The Animas R–1000 Insulin Pump". www.animascorp.com/pump_f_f.html.

Web–Site Brochure dated Jan. 4, 2000. SOOIL–Homepage. "Portable Insulin Pump". www.sooil.com/intro2.htm.

Web–Site Brochure dated Jan. 4, 2000. SOOIL–Homepage. "Portable Insulin Pump". www.sooil.com/product2.htm.

Web–Site Brochure dated Jan. 4, 2000. SOOIL–Homepage. "Portable Insulin Pump". www.sooil.com/product3.htm.

Web–Site Brochure dated Jan. 4, 2000. SOOIL–Homepage. "Portable Insulin Pump". www.sooil.com/product4.htm.

User's Guide for Model 508 Insulin Pump, MiniMed, 8/00, 145 pages.

Copy of PCT International Search Report dated Mar. 4, 2002; 5pp.

International Search Report (PCT/US03/16640).*

* cited by examiner

FLOW CONDITION SENSOR ASSEMBLY FOR PATIENT INFUSION DEVICE

CROSS-REFERENCE TO RELATED APPLICATIONS

The present application is related to U.S. Pat. No. 6,740,059, filed on Aug. 31, 2001 and entitled DEVICES, SYSTEMS AND METHODS FOR PATIENT INFUSION, which is assigned to the assignee of the present application and incorporated herein by reference.

The present application is also a continuation-in-part of U.S. Pat. No. 6,692,457, filed on the same day as the present application, and entitled FLOW CONDITION SENSOR ASSEMBLY FOR PATIENT INFUSION DEVICE, which is assigned to the assignee of the present application and incorporated herein by reference.

FIELD OF THE INVENTION

The present invention relates generally to medical devices, systems and methods, and more particularly to small, low cost, portable infusion devices and methods that are useable to achieve precise, sophisticated, and programmable flow patterns for the delivery of therapeutic liquids such as insulin to a mammalian patient. Even more particularly, the present invention is directed to a fluid flow sensor assembly for an infusion device and a method of determining fluid flow in an infusion device.

BACKGROUND OF THE INVENTION

Today, there are numerous diseases and other physical ailments that are treated by various medicines including pharmaceuticals, nutritional formulas, biologically derived or active agents, hormonal and gene based material and other substances in both solid or liquid form. In the delivery of these medicines, it is often desirable to bypass the digestive system of a mammalian patient to avoid degradation of the active ingredients caused by the catalytic enzymes in the digestive tract and liver. Delivery of a medicine other than by way of the intestines is known as parenteral delivery. Parenteral delivery of various drugs in liquid form is often desired to enhance the effect of the substance being delivered, insuring that the unaltered medicine reaches its intended site at a significant concentration. Also, undesired side effects associated with other routes of delivery, such as systemic toxicity, can potentially be avoided.

Often, a medicine may only be available in a liquid form, or the liquid version may have desirable characteristics that cannot be achieved with solid or pill form. Delivery of liquid medicines may best be accomplished by infusing directly into the cardiovascular system via veins or arteries, into the subcutaneous tissue or directly into organs, tumors, cavities, bones or other site specific locations within the body.

Parenteral delivery of liquid medicines into the body is often accomplished by administering bolus injections using a needle and reservoir, or continuously by gravity driven dispensers or transdermal patch technologies. Bolus injections often imperfectly match the clinical needs of the patient, and usually require larger individual doses than are desired at the specific time they are given. Continuous delivery of medicine through gravity feed systems compromise the patient's mobility and lifestyle, and limit the therapy to simplistic flow rates and profiles. Transdermal patches have special requirements of the medicine being delivered, particularly as it relates to the molecular structure, and similar to gravity feed systems, the control of the drug administration is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. An example of a use of an ambulatory infusion pump is for the delivery of insulin for the treatment of diabetes mellitus. These pumps can deliver insulin on a continuous basal basis as well as a bolus basis as is disclosed in U.S. Pat. No. 4,498,843 to Schneider et al.

The ambulatory pumps often work with a reservoir to contain the liquid medicine, such as a cartridge, a syringe or an IV bag, and use electromechanical pumping or metering technology to deliver the medication to the patient via tubing from the infusion device to a needle that is inserted transcutaneously, or through the skin of the patient. The devices allow control and programming via electromechanical buttons or switches located on the housing of the device, and accessed by the patient or clinician. The devices include visual feedback via text or graphic screens, such as liquid crystal displays known as LCD's, and may include alert or warning lights and audio or vibration signals and alarms. The device can be worn in a harness or pocket or strapped to the body of the patient.

Currently available ambulatory infusion devices are expensive, difficult to program and prepare for infusion, and tend to be bulky, heavy and very fragile. Filling these devices can be difficult and require the patient to carry both the intended medication as well as filling accessories. The devices require specialized care, maintenance, and cleaning to assure proper functionality and safety for their intended long term use. Due to the high cost of existing devices, healthcare providers limit the patient populations approved to use the devices and therapies for which the devices can be used.

Clearly, therefore, there was a need for a programmable and adjustable infusion system that is precise and reliable and can offer clinicians and patients a small, low cost, lightweight, easy-to-use alternative for parenteral delivery of liquid medicines.

In response, the applicant of the present application provided a small, low cost, light-weight, easy-to-use device for delivering liquid medicines to a patient. The device, which is described in detail in co-pending U.S. application Ser. No. 09/943,992, filed on Aug. 31, 2001, includes an exit port, a dispenser for causing fluid from a reservoir to flow to the exit port, a local processor programmed to cause a flow of fluid to the exit port based on flow instructions from a separate, remote control device, and a wireless receiver connected to the local processor for receiving the flow instructions. To reduce the size, complexity and costs of the device, the device is provided with a housing that is free of user input components, such as a keypad, for providing flow instructions to the local processor.

Such devices for delivering liquid medicines to a patient, however, are preferably monitored during operation to ensure the maximum benefit to the patient and to ensure the patient's safety. In particular, ensuring the proper and intended flow of fluid from such a device is important. For example, the delivery of the liquid medicine should not be interrupted by a blockage in the flow path or tubing, i.e., occlusion, that delivers the liquid medicine to the patient. An occlusion may interfere with the accurate administration of the liquid medicine to the patient, and should be prevented or detected. Monitoring a fluid delivery device for occlusions during operation, therefore, is preferred.

What is still desired are new and improved devices for delivering fluid to a patient. Preferably, the fluid delivery devices will be simple in design, and inexpensive and easy to manufacture, in order to further reduce the size, complexity and costs of the devices, such that the devices lend themselves to being small and disposable in nature. In addition, the fluid delivery device will preferably include a flow condition sensor assembly for monitoring the delivery of fluid to a patient, and for ensuring that unwanted flow conditions such as occlusions or an empty fluid reservoir, are quickly detected.

SUMMARY OF THE INVENTION

The present invention provides a device for delivering fluid, such as insulin for example, to a patient. The device includes an exit port assembly adapted to connect to a transcutaneous patient access tool, a flow path extending from the exit port assembly, and a flow condition sensor assembly for determining and monitoring the condition of fluid flow within the flow path. The sensor assembly includes a resilient diaphragm having opposing first and second surfaces, with the first surface positioned against the flow path, a chamber wall positioned adjacent the second surface of the diaphragm and defining a sensor chamber adjacent the second surface of the diaphragm, and at least one sensor arranged to provide a threshold signal when the second surface of the diaphragm expands into the chamber in response to at least one predetermined fluid flow condition occurring in the flow path.

The sensor includes a first electrode secured on the second surface of the diaphragm, a second electrode positioned in a fixed location with respect to the first electrode, and an impedance meter connected between the first and the second electrodes.

According to one aspect of the present invention, the predetermined fluid flow condition is one of an occlusion in the flow path, a low flow of fluid in the flow path, a high flow of fluid in the flow path, and a desired flow of fluid in the flow path. According to another aspect, the chamber has a predetermined volume. According to a further aspect, the diaphragm comprises a thin, flat piece of flexible and resilient material.

According to still another aspect of the present invention, the flow condition sensor assembly includes an alarm connected to the sensor. According to one aspect, the alarm is adapted to be activated upon the sensor providing the threshold signal.

According to yet another aspect of the present invention, a processor is connected to the sensor, an alarm is connected to the processor, and the processor is programmed to activate the alarm upon receiving the threshold signal from the sensor. According to a further aspect, the processor is programmed to activate the alarm upon receiving the threshold signal from the sensor for more than a predetermined period. According to another aspect, the processor is programmed to activate the alarm upon receiving the threshold signal from the sensor for less than a predetermined period.

According to a further aspect of the present invention, a processor is connected to the sensor of the sensor assembly, and the processor is programmed to provide a signal indicative of an undesired flow condition upon receiving the threshold signal from the sensor. According to a further aspect, the processor is programmed to provide a signal indicative of an occluded flow condition upon receiving the threshold signal from the sensor for more than a predetermined period. According to another aspect, the processor is programmed to provide a signal indicative of a low flow condition upon receiving the threshold signal from the sensor for less than a predetermined period.

The present invention provides another device for delivering fluid, such as insulin for example, to a patient. The device includes an exit port assembly adapted to connect to a transcutaneous patient access tool, a flow path extending from the exit port assembly, and a flow condition sensor assembly for determining and monitoring the condition of fluid flow within the flow path. The sensor assembly includes a resilient diaphragm having opposing first and second surfaces, with the first surface positioned against the flow path, a chamber wall positioned adjacent the second surface of the diaphragm and defining a sensor chamber adjacent the second surface of the diaphragm. The chamber wall is contoured such that the chamber includes at least two sections. At least one sensor is arranged in each section of the chamber to provide a threshold signal when the second surface of the diaphragm expands into the section in response to at least one predetermined fluid flow condition occurring in the flow path.

These aspects of the invention together with additional features and advantages thereof may best be understood by reference to the following detailed descriptions and examples taken in connection with the accompanying illustrated drawings.

BRIEF DESCRIPTION OF THE DRAWINGS

Like reference characters designate identical or corresponding components and units throughout the several views.

DETAILED DESCRIPTION OF THE PREFERRED EMBODIMENTS

Figure 2:
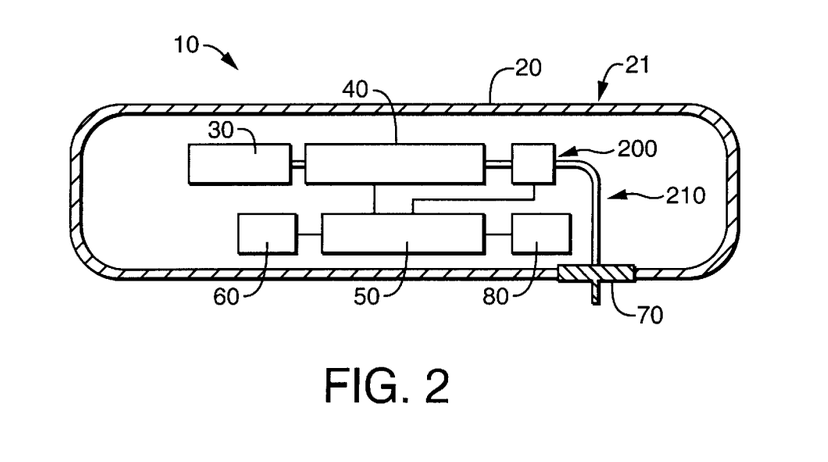
FIG. 2 is a sectional side view of the fluid delivery device of FIG. 1 including an exemplary embodiment of a flow condition sensor assembly constructed in accordance with the present invention.

Referring first to FIG. 2, there is illustrated a fluid delivery device 10 including a flow condition sensor assembly 200 constructed in accordance with the present invention. The flow condition sensor 200 monitors flow conditions within a flow path 210 during operation of the device 10, to ensure that fluid is being delivered as intended. The flow path 210 of the fluid delivery device 10 generally includes a reservoir 30, an exit port assembly 70 adapted to connect to, or include a transcutaneous patient access tool such as a needle (not shown), and a dispenser 40 for causing fluid from the reservoir 30 to flow to the exit port assembly 70.

The types of flow conditions to be monitored by the sensor assembly 200 can include, but are not limited to, an occlusion in the flow path 210, an inadequate flow of fluid in the flow path (due to an empty reservoir for example), and an adequate flow of fluid in the flow path. As discussed below, the sensor assembly provides the benefit, among others, of being volume-based, as opposed to simply being pressure-based for example. A description of the fluid delivery device 10, however, is first provided.

The fluid delivery device 10 of FIG. 2 can be used for the delivery of fluids to a person or animal. The types of liquids that can be delivered by the fluid delivery device 10 include, but are not limited to, insulin, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics. The types of medical conditions that the fluid delivery device 10 might be used to treat include, but are not limited to, diabetes, cardiovascular disease, pain, chronic pain, cancer, AIDS, neurological diseases, Alzheimer's Disease, ALS, Hepatitis, Parkinson's Disease or spasticity. In addition, it should be understood that the flow condition sensor assembly 200 according to the present invention can be used with fluid delivery devices other than those used for the delivery of fluids to persons or animals.

Figure 1:
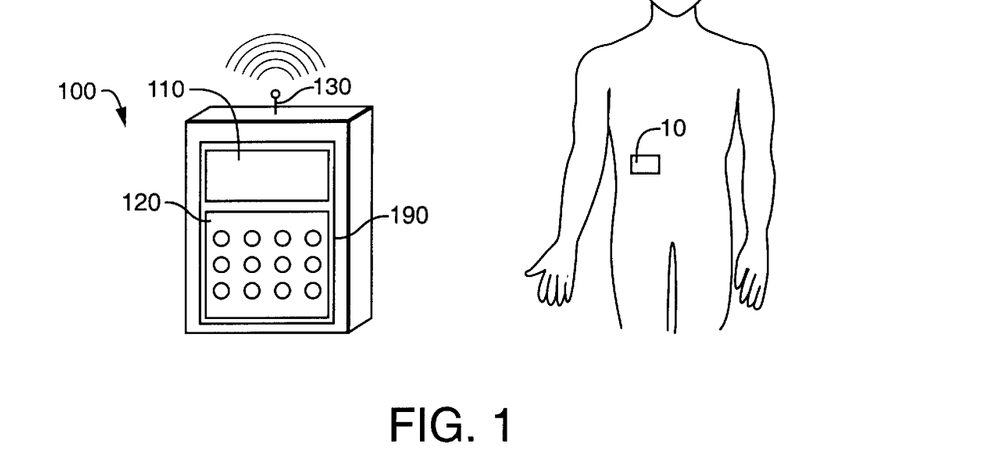
FIG. 1 is a perspective view of a first exemplary embodiment of a fluid delivery device in accordance with this invention shown secured on a patient, and a remote control device for use with the fluid delivery device (the remote control device being enlarged with respect to the patient and the fluid delivery device for purposes of illustration)

The fluid delivery device 10 also includes a processor or electronic microcontroller (hereinafter referred to as the "local" processor) 50 connected to the dispenser 40. The local processor 50 is programmed to cause a flow of fluid to the exit port assembly 70 based on flow instructions from a separate, remote control device 100, an example of which is shown in FIG. 1. Referring also to FIG. 2, the fluid delivery device 10 further includes a wireless receiver 60 connected to the local processor 50 for receiving the flow instructions from the separate, remote control device 100 and delivering the flow instructions to the local processor. The device 10 also includes a housing 20 containing the exit port assembly 70, the reservoir 30, the dispenser 40, the local processor 50, the wireless receiver 60, and the flow condition sensor assembly 200.

As shown, the housing 20 of the fluid delivery device 10 is free of user input components for providing flow instructions to the local processor 50, such as electromechanical switches or buttons on an outer surface 21 of the housing, or interfaces otherwise accessible to a user to adjust the programmed flow rate through the local processor 50. The lack of user input components allows the size, complexity and costs of the device 10 to be substantially reduced so that the device 10 lends itself to being small and disposable in nature. Examples of such devices are disclosed in co-pending U.S. patent application Ser. No. 09/943,992, filed on Aug. 31, 2001 (Atty. Docket No. INSL-110), and entitled DEVICES, SYSTEMS AND METHODS FOR PATIENT INFUSION, which is assigned to the assignee of the present application and has previously been incorporated herein by reference.

In order to program, adjust the programming of, or otherwise communicate user inputs to the local processor 50, the fluid delivery device 10 includes the wireless communication element, or receiver 60 for receiving the user inputs from the separate, remote control device 100 of FIG. 1. Signals can be sent via a communication element (not shown) of the remote control device 100, which can include or be connected to an antenna 130, shown in FIG. 1 as being external to the device 100.

The remote control device 100 has user input components, including an array of electromechanical switches, such as the membrane keypad 120 shown. The control device 100 also includes user output components, including a visual display, such as a liquid crystal display (LCD) 110. Alternatively, the control device can be provided with a touch screen for both user input and output. Although not shown in FIG. 1, the remote control device 100 has its own processor (hereinafter referred to as the "remote" processor) connected to the membrane keypad 120 and the LCD 110. The remote processor receives the user inputs from the membrane keypad 120 and provides "flow" instructions for transmission to the fluid delivery device 10, and provides information to the LCD 110. Since the remote control device 100 also includes a visual display 110, the fluid delivery device 10 can be void of an information screen, further reducing the size, complexity and costs of the device 10.

The communication element 60 of the device 10 preferably receives electronic communication from the remote control device 100 using radio frequency or other wireless communication standards and protocols. In a preferred embodiment, the communication element 60 is a two-way communication element, including a receiver and a transmitter, for allowing the fluid delivery device 10 to send information back to the remote control device 100. In such an embodiment, the remote control device 100 also includes an integral communication element comprising a receiver and a transmitter, for allowing the remote control device 100 to receive the information sent by the fluid delivery device 10.

The local processor 50 of the device 10 contains all the computer programs and electronic circuitry needed to allow a user to program the desired flow patterns and adjust the program as necessary. Such circuitry can include one or more microprocessors, digital and analog integrated circuits, resistors, capacitors, transistors and other semiconductors and other electronic components known to those skilled in the art. The local processor 50 also includes programming, electronic circuitry and memory to properly activate the dispenser 40 at the needed time intervals.

In the exemplary embodiment of FIG. 2, the device 10 includes a power supply 80, such as a battery or capacitor, for supplying power to the local processor 50. The power supply 80 is preferably integrated into the fluid delivery device 10, but can be provided as replaceable, e.g., a replaceable battery.

Although not shown, the device 10 can include sensors or transducers such as a reservoir volume transducer or a reservoir pressure transducer, for transmitting information to the local processor 50 to indicate how and when to activate the dispenser 40, or to indicate other parameters determining flow, pump flow path prime condition, blockage in flow path, contact sensors, rotary motion or other motion indicators, as well as conditions such as the reservoir 30 being empty or leaking, or the dispensing of too much or too little fluid from the reservoir, etc.

The volume of the reservoir 30 is chosen to best suit the therapeutic application of the fluid delivery device 10 impacted by such factors as available concentrations of medicinal fluids to be delivered, acceptable times between refills or disposal of the fluid delivery device 10, size constraints and other factors. The reservoir 30 may be prefilled by the device manufacturer or a cooperating drug manufacturer, or may include external filling means, such as a fill port having needle insertion septum or a Luer connector, for example. In addition, the device 10 can be provided with a removable reservoir.

The exit port assembly 70 can include elements to penetrate the skin of the patient, such that the entire volume of the flow path 210 of the fluid delivery device 10 is predetermined. For example, a needle-connection tubing terminating in a skin penetrating cannula (not shown) can be provided as an integral part of the exit port assembly 70, with the skin penetrating cannula comprising a rigid member, such as a needle. The exit port assembly 70 can further be provided with injection means, such as a spring driven mechanism, to assist in penetrating the skin with the skin penetrating cannula. For example, if the cannula is a flexible tube, a rigid penetrator within the lumen of the tube can be driven through the skin by the injection means and then withdrawn, leaving the soft cannula in place in the subcutaneous tissue of the patient or other internal site. The injection means may be integral to the device 10, or removable soon after transcutaneous penetration.

Alternatively, the exit port assembly 70 can be adapted to connect, with a Luer connector for example, to a separate, standard infusion device that includes a skin penetrating cannula. In any event, the exit port assembly 70 can also be provided with a removable plug (not shown) for preventing leakage during storage and shipment if pre-filled, and during priming if filled by user, and prior to use. It should be understood that, as used herein, the term "flow path" is meant to include all portions of the fluid delivery device 10 that contain therapeutic fluid for delivery to a patient, e.g., all portions between the fill port of the reservoir to the tip of the needle of the exit port assembly.

The device 10 can also be provided with an adhesive layer on the outer surface of the housing 20 for securing the device 10 directly to the skin of a patient, as shown in FIG. 1. Although not shown, the adhesive layer is preferably provided in a continuous ring encircling the exit port assembly 70 in order to provide a protective seal around the penetrated skin. The housing 20 can be made from flexible material, or can be provided with flexible hinged sections that allow the fluid delivery device 10 to flex during patient movement to prevent detachment and aid in patient comfort.

In the exemplary embodiment of FIG. 2, the device 10 is provided with a pressurized reservoir 30, and the dispenser 40 is adapted to control flow from the reservoir 30. The dispenser 40 does not create a driving or pumping force on the fluid passing therethrough, but rather acts as a metering device, allowing pulses of fluid to pass from the pressurized reservoir 30, through the dispenser 40, to the exit port assembly 70. Examples of such "metering" dispensers are shown in co-pending U.S. patent application Ser. No. 09/977,434, filed Oct. 12, 2001 (Atty. Docket No. INSL-116), and entitled LAMINATED PATIENT INFUSION DEVICE, which is assigned to the assignee of the present application and incorporated herein by reference. It should be understood, however, that "driving or pumping" type dispensers can also be used with a device incorporating a sensor assembly 200 of the present invention. Examples of such "driving or pumping" dispensers are shown in co-pending U.S. patent application Ser. No. 09/955,623, filed on Sep. 19, 2001 (Atty. Docket No. INSL-117), and entitled PLUNGER FOR PATIENT INFUSION DEVICE, which is assigned to the assignee of the present application and incorporated herein by reference. In any event, the dispenser 40 is controlled by the local processor 50, which includes electronic programming, controls, and circuitry to allow sophisticated fluid delivery programming and control of the dispenser 40.

Figure 3:
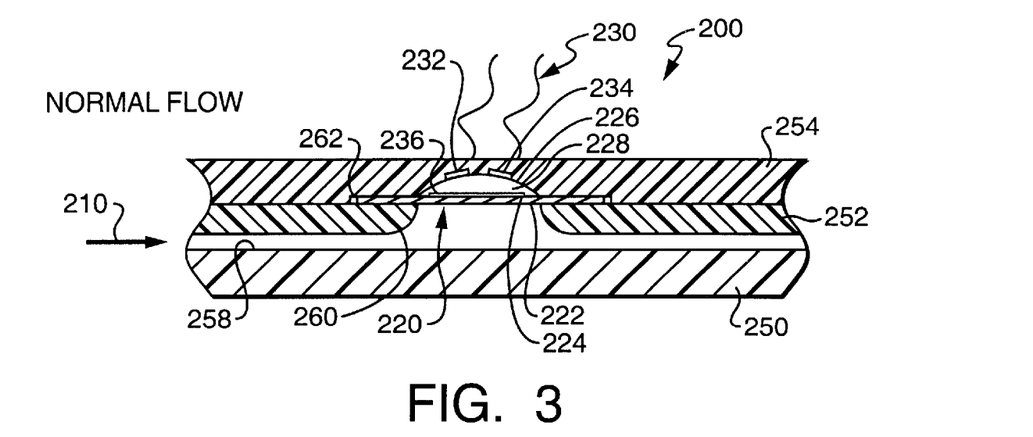
FIG. 3 is a sectional side view of the flow condition sensor assembly of the fluid delivery device of FIG. 2, illustrating operation of the assembly during a flow condition comprising normal flow.
Figure 4:
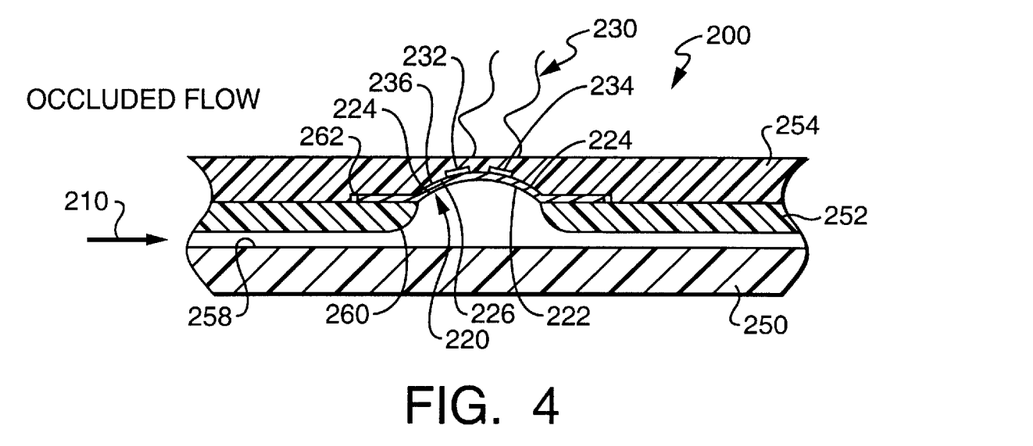
FIG. 4 is a sectional side views of the flow condition sensor assembly of FIGS. 2 and 3, illustrating operation of the assembly during a flow condition comprising an occlusion.

Referring now to FIGS. 3 and 4, an exemplary embodiment of the flow condition sensor assembly 200 of the present invention is shown. The sensor assembly 200 generally includes a resilient diaphragm 220 having opposing first and second surfaces 222, 224, with the first surface 222 positioned against the flow path 210 of the device 10, and a chamber wall 226 positioned adjacent the second surface 224 of the diaphragm. The diaphragm 220 is made from a suitably expandable yet resilient material, such as rubber or a synthetic rubber. The chamber wall 226 is adapted such that an enclosed chamber 228 is defined between the chamber wall 226 and the second surface 224 of the diaphragm 220. Preferably, the chamber 228 is provided with a predetermined volume. Although not shown, the chamber 228 can also be provided with a relief port for allowing air to escape the chamber upon expansion of the diaphragm 220.

The diaphragm 220 and the chamber 228 are arranged and adapted such that during a normal flow condition and between flow pulses, the flow of fluid through the flow path 210 does not cause the diaphragm 220 to expand into the chamber 228, as illustrated in FIG. 3. The diaphragm 220 and the chamber 228 are also arranged and adapted such that during a normal flow condition, the flow of fluid through the flow path 210 causes the diaphragm 220 to expand fully into the chamber 228 for about a predetermined period. During an occluded flow condition (downstream occlusion), the diaphragm 220 expands fully into the chamber, as illustrated in FIG. 4, for more than the predetermined period. During a low flow condition (due to an upstream occlusion, a fluid leak, or an empty reservoir for example), the diaphragm 220 may expand fully into the chamber, but for less than the predetermined period, or may not expand into the chamber.

In any event, the diaphragm 220 and the chamber 228 are arranged and adapted such that the amount of expansion and the duration of the expansion of the diaphragm into the chamber can be used to determine the flow condition within the flow path 210.

The sensor assembly 200 also includes at least one sensor 230 arranged to provide a signal when the second surface 224 of the diaphragm 220 expands into the chamber 228 in response to at least one predetermined fluid flow condition occurring in the flow path 210. For example, the sensor 230 can be arranged to determine when the second surface 224 of the diaphragm 220 expands fully into the chamber 228 and contacts the chamber wall 226, as illustrated in FIG. 4. Alternatively, the specific magnitudes of expansion of the diaphragm 220 into the chamber 228 can correlate to an analog signal representing various flow conditions.

The sensor 230 can comprise any device for determining and providing an indication of the position of the diaphragm 220 in the chamber 228. For example, the sensor can comprises one of a conductive film such as a metallic layer or coating, a contact or pressure switch, a magnetic Hall effect sensor, a strain gage, and a density gage. In the embodiment of FIGS. 3 and 4, the sensor comprises an open circuit 230 having two leads 232, 234. The sensor 230 also includes a conductive coating 236 on the second surface 224 of the diaphragm 220. During full expansion of the diaphragm 220 into the chamber 228, the conductive coating 236 eventually contacts both leads 232, 234, and closes the circuit 230.

In the embodiment 200 of the invention illustrated in FIG. 2, the processor 50 of the fluid delivery device 10 also acts as the processor for the sensor assembly 200 and is connected to the open circuit 230. During full expansion of the diaphragm 220 into the chamber 228, the circuit 230 is closed to provide a "signal" to the processor 50.

Alternatively, the sensor assembly 200 can be provided with its own, separate processor programmed to operate in accordance with the present invention. In addition, the sensor 230 can simply be connected to an alarm, such as a light emitting diode or an electronic sound maker, and which is activated upon the circuit of the sensor 230 being closed upon a predetermined flow condition, such as an occlusion. In this manner, a user can simply receive a visual or an audible alarm signal upon full expansion of the diaphragm 220 into the chamber 228 to close the circuit 230.

Figures 5A, 5B:
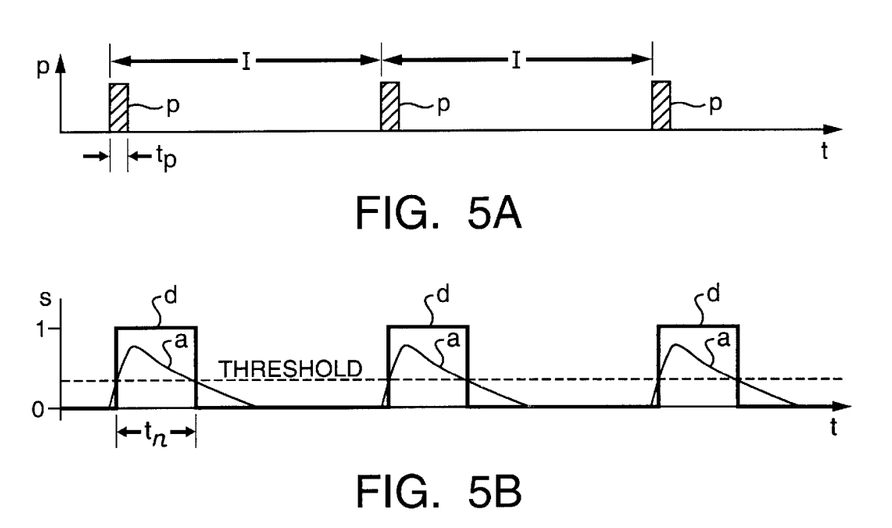
FIG. 5a is a graph of pressure versus time illustrating pulses of fluid flow within a flow path of the fluid delivery device of FIGS. 1 and 2.
FIG. 5b is a graph of signal strength versus time, shown in both digital and analog form, from the flow condition sensor assembly of FIGS. 2 through 4 correlating to the pulses of fluid flow within the flow path of the device for a flow condition comprising a normal fluid flow.

FIGS. 5a through 5d illustrate an exemplary embodiment of a method of determining flow conditions according to the present invention and as carried out by the processor 50. FIG. 5a is a graph of pressure versus time illustrating pulses "p" of fluid flow within the flow path 210 of the fluid delivery device 10 of FIGS. 1 and 2 as produced by the dispenser 40 during normal operation. As shown, pulses "p" occur at predetermined intervals "I" and each pulse "p" lasts for a predetermined pulse period "$t_p$". FIG. 5b is a graph of signal strength versus time, shown in both digital form "d" and analog form "a", from the flow condition sensor assembly 200 of FIGS. 2 through 4, correlating to the pulses "p" of fluid flow within the flow path 210 of the device 10 for a flow condition comprising a normal fluid flow. As shown, the digital signal "d", which are based on predetermined "threshold" levels of the analog signals "a", each lasts for a predetermined normal period "$t_n$". The processor 50 can be provided with an analog-to-digital converter for converting the analog signals "a" from the sensor 230 to digital signals "d".

Figure 5C:
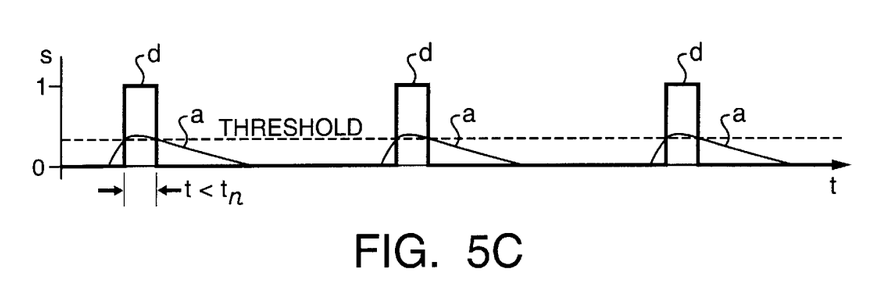
FIG. 5c is a graph of signal strength versus time, shown in both digital and analog form, from the flow condition sensor assembly of FIGS. 2 through 4 correlating to the pulses of fluid flow within the flow path of the device for a flow condition comprising a low fluid flow.
Figure 5D:
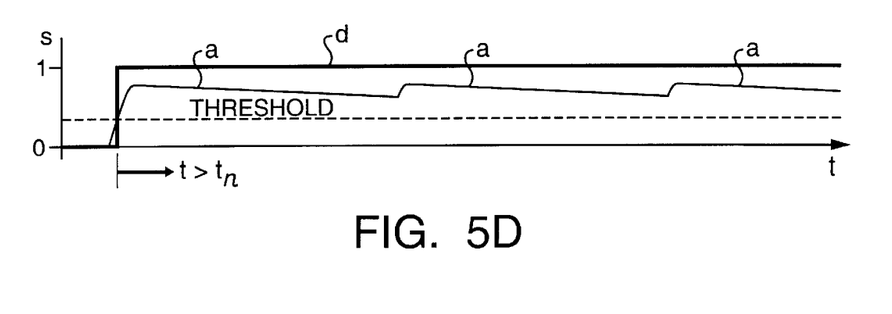
FIG. 5d is a graph of signal strength versus time, shown in both digital and analog form, from the flow condition sensor assembly of FIGS. 2 through 4 correlating to the pulses of fluid flow within the flow path of the device for a flow condition comprising an occluded fluid flow.

FIG. 5c is a graph of signal strength versus time correlating to the pulses of fluid flow within the flow path 210 of the device 10 for a flow condition comprising a low fluid flow. A low flow condition might occur, for example, when the reservoir becomes empty. As shown, each digital signal "d" lasts for a period "t" less than the predetermined normal period "$t_n$". FIG. 5d is a graph of signal strength versus time correlating to the pulses of fluid flow within the flow path 210 of the device 10 for a flow condition comprising an occluded fluid flow. As shown, the digital signals "d" last for a period "t" greater then the predetermined normal period "$t_n$".

The analog signals "a" illustrated in FIGS. 5b through 5d are produced upon the second surface 224 of the diaphragm 220 expanding fully into the chamber 228 and closing the sensor circuit 230, as illustrated in FIG. 4. Upon receiving signals "a" such as those illustrated in FIGS. 5c and 5d, the processor 50 is programmed to send an "undesired flow condition" signal to the remote control device 100 to warn a user that the flow delivery device 10 is not producing a desired flow condition. Although not shown, the remote control device 100 can include an alarm, such as an audible or visual alarm, that the remote processor of the remote control device 100 activates upon receiving the "undesired flow condition" signal from the local processor 50. In addition, the fluid delivery device 10 can be provided with an alarm, such as a light emitting diode or electronic buzzer, connected to the local processor 50 for activation during an undesired flow condition. In any event, since the delivery device 10 is not producing the desired flow condition, the user may not be receiving the proper amount of medication, or other fluid, and is therefore warned. Because the fluid delivery device 10 of the present invention is preferably disposable and relatively inexpensive, the user can simply dispose of the fluid delivery device 10 with the "undesired flow condition" and begin using a new fluid delivery device 10.

Because the chamber 228 of the sensor assembly 200 is provided with a predetermined volume, a user is more quickly able to determine the occurrence of an undesired flow condition. Most existing occlusion sensor devices monitor pressure to determine flow conditions. The present invention, in contrast, determines an occlusion condition on a volume "not infused". A low occlusion volume correlates to low volume "not infused" prior to the alarm being activate. A low occlusion volume also corresponds to low volume infused if the occlusion is corrected and proper fluid flow restored. This low volume has the clinical benefit of both early detection (amount of fluid not infused to patient prior to alarm state) as well as a low "bolus" volume in the cases where the occlusion is removed (such as the case where kinked tubing causes the occlusion and the kink is removed—"dumping" up to that volumetric amount into the patient almost immediately).

The preferred volume of the chamber must take into account the compliance of the entire flow path 210 of system 10. At relative infusion and occlusion pressures, the flow path 210 may expand, thereby artificially adding to the volume of the sensor chamber. Any such artificially expanded volume must be taken into account in monitoring the signals received from the sensor. Preferably, the flow path 210 is designed to have minimal compliance at both normal operating pressures and abnormal operating pressures. If minimal compliance of the flow path is not possible, however, the computer algorithm of the processor can be programmed to take the known compliance of the flow path 210 into account when determining flow conditions based upon signals received from the sensor.

In one possible embodiment of the invention, one of the local processor 50 and the remote processor is programmed to note the time when a "undesired flow condition" signal is received, such that a user knows when an undesired flow condition began.

In another exemplary embodiment, the processor is provided with a software algorithm for avoiding "occlusion detection" during pumping, by instructing the processor to check for occlusion when actual pumping by the dispenser has ceased. The processor can also be programmed to check for proper flow conditions during an initial priming function of the fluid flow device 10. If the processor determines through the sensor assembly that the fluid delivery device is not producing a desired flow condition, the processor is programmed to shut the fluid delivery device down and signal an alarm before attachment of the fluid delivery device to a patient.

Referring back to FIGS. 3 and 4, the exemplary embodiment of the sensor assembly is constructed from at least two laminated layers 250, 252, 254 of material in addition to the diaphragm 220. The layers 250, 252, 254 can be made from a suitably strong and rigid material such as plastic or stainless steel, and can be secured together in a suitable manner, such as with adhesives or by welding. The laminated construction provides many benefits including, but not limited to, simplifying the design and manufacturing of the sensor assembly 200, and further reducing the size, complexity and costs of the fluid delivery device 10. The sensor assembly 200 of the present invention, therefore, lends itself to being small and disposable in nature.

In the embodiment of FIGS. 3 and 4, the layers of the sensor assembly include a first layer 250 and a second layer 252 received against the first layer. At least one of the second and the first layers 250, 252 includes a surface groove 258 between the layers which forms part of the flow path 210 of the fluid delivery device 10 connected between the dispenser 40 and the exit port assembly 70. The second layer 252 includes an opening 260 in fluid communication with the passageway. The resilient diaphragm 220 is received on the second layer 254 covering the opening 260, and a third layer 256 is received over the diaphragm 220 on the second layer. The third layer 256 forms the chamber wall 226 that defines the chamber 228 over the diaphragm 220 and in alignment with the opening 260 of the second layer 252.

The laminated construction of the sensor assembly 200 allows most manufacturing tolerances of the sensor assembly 200 to be lowered, and the manufacturing process to be simplified, without effecting the performance and reliability of the sensor assembly 200. A relatively high tolerance is required for only the volume of the chamber 228. Other dimensions and properties of the sensor assembly 200 can be relatively relaxed to reduce the costs of the assembly. For example, in the embodiment shown, at least one of the second and the third layers 252, 254 defines a recess 262 receiving the diaphragm 220. The recess 262 has a depth about equal to a thickness of the diaphragm 220 such that the diaphragm 220 is secured in a substantially fluid-tight manner between the second and the third layers 252, 254. However, a length and a width of the recess 262 are greater than a length and a width of the diaphragm 220 in order to decrease the required manufacturing tolerances of the sensor assembly 200. A resilience of the diaphragm 220 does not require a relatively high tolerance, as long as the resilience of the diaphragm is great enough to force fluid out of the chamber 228 between normal, non-occluded pulses, yet flexible enough to expand into the chamber during an occluded flow.

In alternative embodiments, the diaphragm can be provided as other than a flat layer 220 of resiliently expandable material. The diaphragm can include any structure that provides a fluid-tight barrier between the flow path 210 and the sensor chamber 228, and that moves into the chamber upon an increase in pressure in the flow path. For example, the diaphragm may be provided as a piston biased away from the chamber wall with a spring. Many alternative embodiments of the diaphragm are possible while remaining within the scope of the present invention.

In an alternative embodiment of the sensor assembly of the present invention, the sensor assembly is positioned at the end of a reservoir in a fluid delivery device including a "driving or pumping" type dispenser. As previously discussed, examples of such "driving or pumping" dispensers are shown in co-pending U.S. patent application Ser. No. 09/955,623, filed on Sep. 19, 2001 (Atty. Docket No. INSL-117), and entitled PLUNGER FOR PATIENT INFUSION DEVICE. Positioning the sensor assembly at the end of a reservoir opposite the dispenser simplifies the manufacturing process of the sensor assembly and the fluid delivery device and can reduce the number of parts to be assembled.

Figure 6:
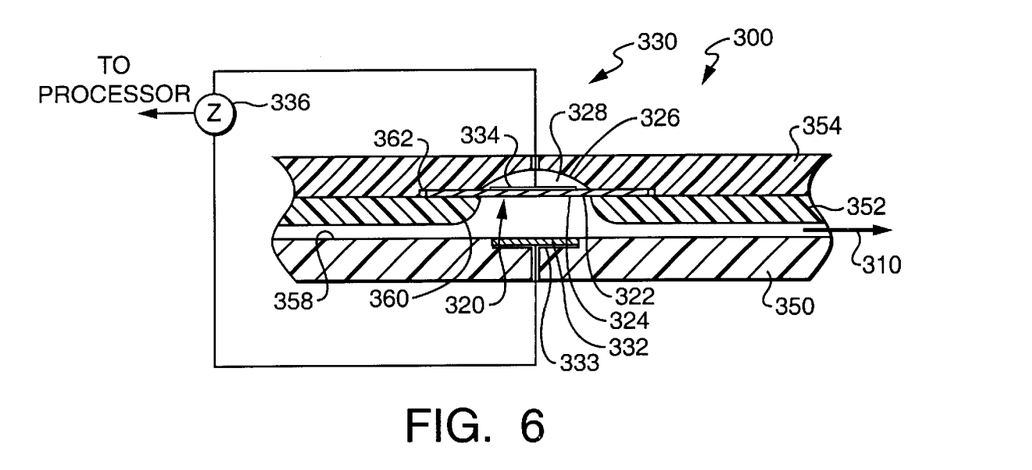
FIGS. 6 and 7 are sectional sides views of another exemplary embodiment of a flow condition sensor assembly constructed in accordance with the present invention, illustrating operation of the assembly during two flow conditions.
Figure 7:
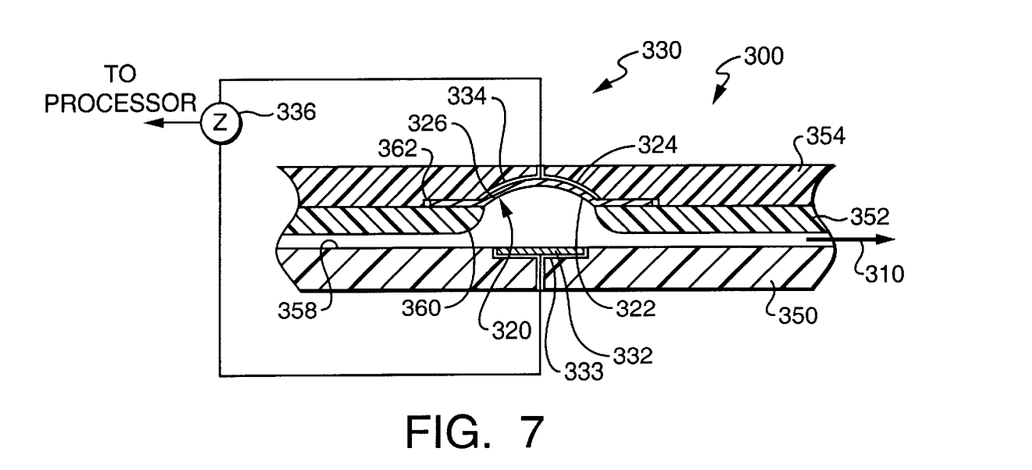

FIGS. 6 and 7 are sectional side views of another exemplary embodiment of a flow condition sensor assembly 300 constructed in accordance with the present invention, illustrating operation of the assembly during two flow conditions. Operation of the assembly 300 of FIGS. 6 and 7 is similar to operation of the assembly 200 of FIGS. 3 and 4. In addition, some elements of the assembly 300 of FIGS. 6 and 7 are similar to elements of the assembly 200 of FIGS. 3 and 4 such that similar elements have the same reference numeral preceded by a "3". The flow condition sensor assembly 300 of FIGS. 6 and 7, however, includes a capacitive proximity sensor 330 including two electrodes 332, 334 and an impedance meter 336. In addition to sensing movement of the diaphragm 320 into the chamber 328, the capacitive proximity sensor 330 can also be used to detect the presence of bubbles within fluid passing through the flow path 310.

The two electrodes 332, 334 are arranged and adapted such that expansion of the diaphragm 320 into the chamber 328 changes the capacitance between the electrodes 332, 334. The change in capacitance is measured through the impedance meter 336, which is connected to the processor and/or alarm. In the embodiment shown, one of the electrodes 334 is secured to the second surface 324 of the diaphragm 320, while the other electrode 332 is secured in a substantially fluid-tight manner in a recess 333 positioned in a surface of the flow path 310 opposite the diaphragm 320 (alternatively, the other electrode 332 can be secured on the wall of the chamber 328 opposite the diaphragm 320). During expansion of the diaphragm 320 into the chamber 328 due to fluid flow through the flow path 310, the distance between the electrodes 332, 334 changes and can be measured through the impedance meter 336. The processor can be programmed to determine the fluid flow condition within the flow path 310 based upon the magnitude of the changes in impedance as measured by the impedance meter 336, or by both the magnitude and duration of impedance change.

The capacitive proximity sensor 330 can also be used to detect the presence of bubbles within fluid passing through the flow path 310. In general, air bubbles are not desired within fluid to be infused into a patient, since the air bubbles can decrease the volume of fluid actually delivered to the patient. In addition, air bubbles can indicate an unwanted flow condition such as a leak in the flow path 310. Detecting the presence of air bubbles within fluid passing through the flow path 310 can be very useful, therefore, in monitoring fluid flow conditions during operation of the fluid delivery device 10. Air bubbles within fluid within the flow path 310 causes a change in the dielectric constant between the electrodes 332, 334, which in turn is measured through the impedance meter 336. The processor is programmed to determine the presence of air bubbles based on the change in impedance.

Figure 8:
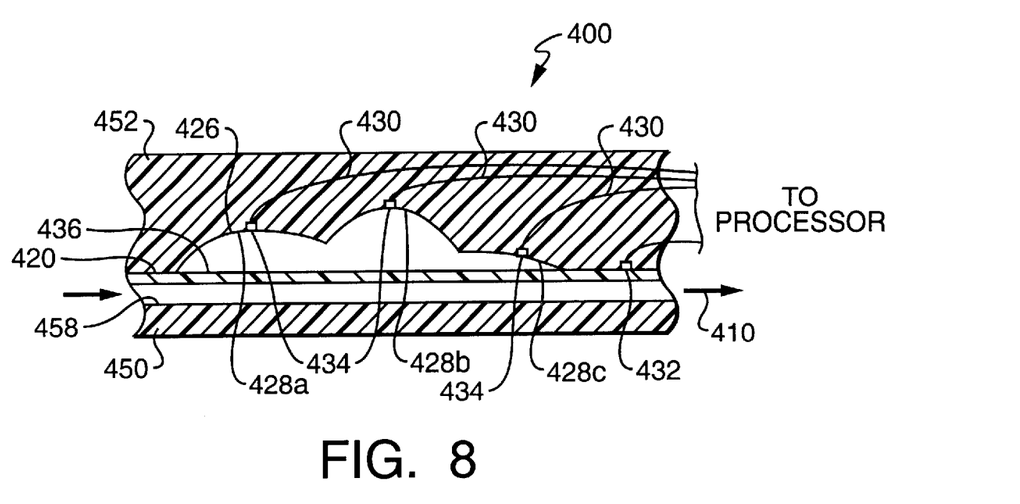
FIGS. 8 and 9 are sectional side views of an additional exemplary embodiment of a flow condition sensor assembly constructed in accordance with the present invention, illustrating operation of the assembly during two flow conditions.
Figure 9:
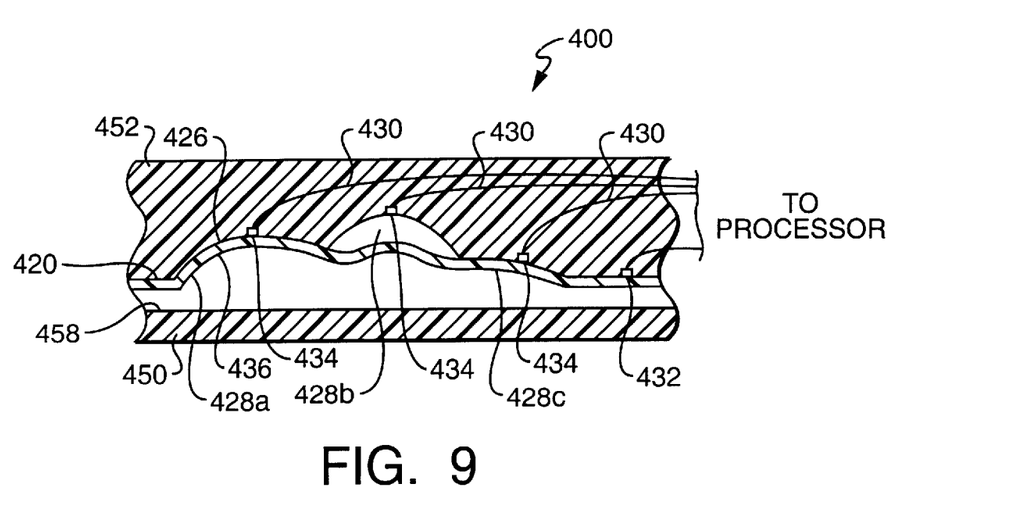

FIGS. 8 and 9 are sectional side views of an additional exemplary embodiment of a flow condition sensor assembly 400 constructed in accordance with the present invention, illustrating operation of the assembly during two flow conditions. Operation of the assembly 400 is similar to operation of the assembly 200 of FIGS. 3 and 4. In addition, elements of the assembly 400 are similar to elements of the assembly 200 of FIGS. 3 and 4 such that similar elements have the same reference numeral preceded by a "4". The flow condition sensor assembly 400, however, includes a chamber wall 426 that is contoured such that the chamber includes at least two distinct sections 428a, 428b, 428c. At least one sensor 430 is positioned in each chamber section 428a, 428b, 428c for providing a signal when the second surface of the diaphragm 420 expands into the corresponding section of the chamber.

In the embodiment shown, the chamber includes three distinct sections 428a, 428b, 428c, and each of the sections has a single sensor 430 positioned therein. Each of the three sensors, in turn, comprises an open circuit 430, and all three circuits share a lead 432 connected to the conductive coating 436 on the second surface 424 of the diaphragm 420. The second leads 434 of each circuit are positioned within the chamber sections 428a, 428b, 428c such that, during expansion of the diaphragm 420 into the corresponding sections 428a, 428b, 428c, the conductive coating 436 contacts the second leads 434 of the circuits 430, closes the circuits 430, and thereby provides corresponding "signals" to the processor and/or alarm connected to the circuits 430.

The second leads 434 are positioned within the chamber sections 428a, 428b, 428c in a predetermined manner, and the chamber sections are each provided with a predetermined volume, such that the closing of one or more of the circuits 430 indicates a particular flow condition. For example, the processor is programmed to determine that an undesired "low" flow condition is occurring if the fluid flow through the flow path 410 causes the diaphragm 420 to expand only into one of the chamber section 428c and cause only the first circuit 430 to close. The processor is also programmed to determine that a desired or "normal" flow condition is occurring if the fluid flow causes the diaphragm 420 to expand into two of the chamber sections 428a, 428c as shown in FIG. 9, and cause the first and the third circuits 430 to close. If the diaphragm 420 expands into all three chamber sections 428a, 428b, 428c and the three circuits 430 are closed, the processor is programmed to determine that an undesired "occlusion" flow condition is occurring.

In relation to multiple "trigger" volumes 428a, 428b, 428c, the detection of low flow, normal flow, occluded flow, as described is one use. Alternatively, each "trigger" volumes 428a, 428b, 428c can be adapted to indicate an occlusion condition, but for different occlusion amounts. These volumes 428a, 428b, 428c can be set to trigger different types of alarms, or the user or clinician may set one of the volumes 428a, 428b, 428c to indicate a preferred occlusion volume. For example, a specific drug, such as insulin, may need to trigger at as low an occlusion volume as possible, while a different drug such as an antibiotic or analgesic, may have a larger occlusion volume as more appropriate. The settings could be preprogrammed at manufacturing (multi-application manufactured pump, specifically sold for one application) or can be selected by the user or clinician prior to use. In addition, the single diaphragm 420 can be provided with different expansion properties along its length.

The exemplary embodiment 400 of FIGS. 8 and 9 includes three chamber sections 428a, 428b, 428c of different volumes. However, it should be understood that the chamber can be provided with two or more sections, and the sections can include the same volumes or different volume. In addition, the flow condition sensor assembly 400 can include more than one sensor 430 in each chamber section 428a, 428b, 428c. Furthermore, the assembly 400 can include sensors other than the open circuits 430, such as sensors responsive to one of contact, pressure, light, magnetic strength, strain, capacitance, inductance, and density. For example, the sensors of FIGS. 8 and 9 can each comprise the capacitive proximity sensor of FIGS. 6 and 7.

As illustrated by the above described exemplary embodiments, the present invention generally provides a device for delivering fluid to a patient including an exit port assembly adapted to connect to a transcutaneous patient access tool, a flow path extending from the exit port assembly, and a flow condition sensor assembly including a resilient diaphragm having opposing first and second surfaces. The first surface of the diaphragm is positioned against the flow path, and a chamber wall is positioned adjacent the second surface of the diaphragm and defines a sensor chamber against the second surface of the diaphragm. At least one sensor is arranged to provide a threshold signal when the second surface of the diaphragm expands into the chamber in response to at least one predetermined fluid flow condition occurring in the flow path. The timing, level and duration of the signals from the sensor are correlated by the local processor to the pumping produced by the dispenser, and used to determine the flow condition.

It should be understood that the embodiments described herein are merely exemplary and that a person skilled in the art may make variations and modifications to the embodiments described without departing from the spirit and scope of the present invention. All such equivalent variations and modifications are intended to be included within the scope of this invention as defined by the appended claims.

What is claimed is:

1. A device for delivering fluid to a patient, comprising:
A) an exit port assembly adapted to connect to a transcutaneous patient access tool;
B) a flow path extending from the exit port assembly; and
C) a flow condition sensor assembly including
   a resilient diaphragm having opposing first and second surfaces, with the first surface positioned against the flow path,
   a chamber wall positioned adjacent the second surface of the diaphragm and defining a sensor chamber adjacent the second surface of the diaphragm, and
   at least one sensor arranged to provide a threshold signal when the second surface of the diaphragm expands into the chamber in response to at least one predetermined fluid flow condition occurring in the flow path, the sensor including,
      a first electrode secured on the diaphragm,
      a second electrode positioned in a fixed location with respect to the first electrode, and
      an impedance meter connected between the first and the second electrodes.

2. A device according to claim 1, wherein the predetermined fluid flow condition comprises one of an occlusion in the flow path, an inadequate flow of fluid in the flow path, and an adequate flow of fluid in the flow path.

3. A device according to claim 1, wherein the flow path includes a reservoir and a passageway providing fluid communication between the reservoir and the exit port assembly, and the flow condition sensor assembly is positioned against the passageway.

4. A device according to claim 1, wherein the second electrode is positioned on a wall of the flow path.

5. A device according to claim 1, wherein the flow condition sensor assembly further comprises at least two laminated layers and the diaphragm is positioned between two of the layers.

6. A device according to claim 5, wherein the at least two laminated layers comprise:
 a first layer;
 a second layer received against the first layer, the second and the first layers including at least one groove defining a passageway of the flow path, the second layer including an opening in fluid communication with the passageway, and wherein the resilient diaphragm is received on the second layer covering the opening; and
 a third layer received over the diaphragm on the second layer, the third layer including the chamber wall defining the chamber over the diaphragm and in alignment with the opening of the second layer.

7. A device according to claim 6, wherein one of the second and the third layers defines a recess receiving the diaphragm, and wherein the recess has a depth about equal to a thickness of the diaphragm such that the diaphragm is secured in a substantially fluid-tight manner between the second and the third layers.

8. A device according to claim 7, wherein a length and a width of the recess are greater than a length and a width of the diaphragm.

9. A device according to claim 1, wherein the diaphragm comprises a thin, flat piece of flexible and resilient material.

10. A device according to claim 1, wherein the sensor chamber has a predetermined volume.

11. A device according to claim 1, wherein the flow condition sensor assembly includes an alarm connected to the impedance meter.

12. A device according to claim 11, wherein the alarm comprises an audible alarm.

13. A device according to claim 11, wherein the alarm comprises a visual alarm.

14. A device according to claim 1, further comprising a processor connected to the impedance meter of the sensor assembly.

15. A device according to claim 14, further comprising an alarm connected to the processor.

16. A device according to claim 15, wherein the alarm comprises an audible alarm.

17. A device according to claim 15, wherein the alarm comprises a visual alarm.

18. A device according to claim 15, wherein the processor is programmed to activate the alarm upon receiving the threshold signal from the impedance meter.

19. A device according to claim 15, wherein the processor is programmed to activate the alarm upon receiving the threshold signal from the impedance meter for more than a predetermined period.

20. A device according to claim 15, wherein the processor is programmed to activate the alarm upon receiving the threshold signal from the impedance meter for less than a predetermined period.

21. A device according to claim 14, wherein the processor is programmed to stop operation upon receiving the threshold signal from the impedance meter.

22. A device according to claim 14, wherein the processor is programmed to stop operation upon receiving the threshold signal from the impedance meter for more than a predetermined period.

23. A device according to claim 14, wherein the processor is programmed to stop operation upon receiving the threshold signal from the impedance meter for less than a predetermined period.

24. A device according to claim 14, wherein the impedance meter provides an analog signal and the processor include an analog-to-digital converter for converting the analog single to a digital signal.

25. A device according to claim 14, wherein the processor is programmed to provide a signal indicative of an undesired flow condition upon receiving the threshold signal from the impedance meter.

26. A device according to claim 14, wherein the processor is programmed to provide a signal indicative of an occluded flow condition upon receiving the threshold signal from the impedance meter for more than a predetermined period.

27. A device according to claim 14, wherein the processor is programmed to provide a signal indicative of a low flow condition upon receiving the threshold signal from the impedance meter for less than a predetermined period.

28. A device according to claim 14, wherein the processor is programmed to receive the threshold signal from the impedance meter when the device is primed.

29. A device according to claim 14, wherein the processor is programmed to determine the presence of bubbles in the flow path based upon the signal received from the impedance meter.

30. A device according to claim 1, wherein the flow path includes a reservoir containing a therapeutic fluid.

31. A device according to claim 30, wherein the therapeutic fluid is insulin.

32. A device according to claim 30, further comprising a fill port connected to the reservoir.

33. A device according to claim 30, wherein the reservoir is pressurized.

34. A device according to claim 1, wherein the exit port assembly includes a transcutaneous patient access tool.

35. A device according to claim 34, wherein the transcutaneous patient access tool comprises a needle.

36. A device according to claim 1, wherein a combined volume of the exit port assembly and the flow path is fixed and predetermined.

37. A device according to claim 1, wherein possible expansion of a combined volume of the exit port assembly and the flow path is relatively small compared with the volume of the sensor chamber.

38. A device according to claim 1, further comprising:
 a dispenser for causing fluid through the flow path to the exit port assembly;
 a local processor connected to the dispenser and programmed to cause fluid flow to the exit port assembly based upon flow instructions;
 a wireless receiver connected to the local processor for receiving flow instructions from a separate, remote control device and delivering the flow instructions to the local processor; and
 a housing containing the flow path, the exit port assembly, the dispenser, the local processor, and the wireless receiver, wherein the housing is free of user input components for providing flow instructions to the local processor.

39. A system including a fluid delivery device according to claim 38, and further comprising a remote control device separate from the fluid delivery device and including:

a remote processor;
user interface components connected to the remote processor for allowing a user to provide flow instructions to the remote processor; and
a transmitter connected to the remote processor for transmitting the flow instructions to the receiver of the fluid delivery device.

40. A device according to claim 1, further comprising:
a dispenser for causing fluid through the flow path to the exit port assembly;
a local processor connected to the dispenser and programmed to cause fluid flow to the exit port assembly based upon flow instructions, and further programmed to provide flow information;
a wireless transmitter connected to the local processor for transmitting the flow information from the local processor to a separate, remote control device; and
a housing containing the flow path, the exit port assembly, the dispenser, the local processor, and the wireless transmitter, wherein the housing is free of user output components for providing the flow information from the local processor to a user.

41. A system including a fluid delivery device according to claim 40 and further comprising a remote control device separate from the fluid delivery device and including:
a remote processor;
user output components connected to the remote processor for allowing a user to receive flow information; and
a receiver connected to the remote processor for receiving the flow information from the transmitter of the fluid delivery device.

42. A system according to claim 41, wherein the remote control device includes an alarm connected to the remote processor.

43. A device for delivering fluid to a patient, comprising:
A) an exit port assembly adapted to connect to a transcutaneous patient access tool;
B) a flow path extending from the exit port assembly; and
C) a flow condition sensor assembly including,
a resilient diaphragm having opposing first and second surfaces, with the first surface positioned against the flow path,
a chamber wall positioned adjacent the second surface of the diaphragm and defining a sensor chamber adjacent the second surface of the diaphragm, the chamber wall having a contour such that the chamber includes at least two distinct sections; and
at least one sensor positioned in each section of the chamber to provide threshold signals when the second surface of the diaphragm expands into the sections in response to predetermined fluid flow conditions occurring in the flow path.

44. A device according to claim 43, wherein the predetermined fluid flow conditions comprise at least one of an occlusion in the flow path, an inadequate flow of fluid in the flow path, and an adequate flow of fluid in the flow path.

45. A device according to claim 43, wherein the flow path includes a reservoir and the flow condition sensor assembly is positioned at an end of the reservoir.

46. A device according to claim 43, wherein the flow path includes a reservoir and a passageway providing fluid communication between the reservoir and the exit port assembly, and the flow condition sensor assembly is positioned against the passageway.

47. A device according to claim 43, wherein the sensors are responsive to one of contact, pressure, light, magnetism, strain, and density.

48. A device according to claim 43, wherein the sensor is positioned on a portions of the chamber sections furthest from the flow path and each section of the chamber has a predetermined volume.

49. A device according to claim 43, wherein the sensors each comprise a circuit having a lead positioned on the second surface of the diaphragm and a lead positioned on the chamber wall.

50. A device according to claim 43, wherein the flow condition sensor assembly further comprises at least two laminated layers and the diaphragm is positioned between two of the layers.

51. A device according to claim 50, wherein the at least two laminated layers comprise:
a first layer;
a second layer received against the first layer, the second and the first layers including at least one groove defining a passageway of the flow path, the second layer including an opening in fluid communication with the passageway, and wherein the resilient diaphragm is received on the second layer covering the opening; and
a third layer received over the diaphragm on the second layer, the third layer including the chamber wall defining the chamber over the diaphragm and in alignment with the opening of the second layer.

52. A device according to claim 51, wherein one of the second and the third layers defines a recess receiving the diaphragm, and wherein the recess has a depth about equal to a thickness of the diaphragm such that the diaphragm is secured in a substantially fluid-tight manner between the second and the third layers.

53. A device according to claim 52, wherein a length and a width of the recess are greater than a length and a width of the diaphragm.

54. A device according to claim 43, wherein the diaphragm comprises a thin, flat piece of flexible and resilient material.

55. A device according to claim 43, wherein each of the sections of the sensor chamber has a predetermined volume.

56. A device according to claim 43, wherein the flow condition sensor assembly includes an alarm connected to each of the sensors.

57. A device according to claim 56, wherein the alarm comprises an audible alarm.

58. A device according to claim 56, wherein the alarm comprises a visual alarm.

59. A device according to claim 43, further comprising a processor connected to each of the sensors of the sensor assembly.

60. A device according to claim 59, further comprising an alarm connected to the processor.

61. A device according to claim 60, wherein the alarm comprises an audible alarm.

62. A device according to claim 60, wherein the alarm comprises a visual alarm.

63. A device according to claim 60, wherein the processor is programmed to activate the alarm upon receiving the threshold signal from all of the sensors.

64. A device according to claim 60, wherein the processor is programmed to activate the alarm upon receiving the threshold signal from all of the sensors for more than a predetermined period.

65. A device according to claim 60, wherein the processor is programmed to activate the alarm upon receiving the threshold signal from only one of the sensors.

66. A device according to claim 60, wherein the processor is programmed to activate the alarm upon receiving the threshold signal from only one of the sensors for less than a predetermined period.

67. A device according to claim 59, wherein each of the sensors provides an analog signal and the processor include an analog-to-digital converter for converting the analog singles into digital signals.

68. A device according to claim 59, wherein the processor is programmed to provide a signal indicative of an occluded flow condition upon receiving the threshold signal from all of the sensors.

69. A device according to claim 59, wherein the processor is programmed to provide a signal indicative of an occluded flow condition upon receiving the threshold signal from all of the sensors for more than a predetermined period.

70. A device according to claim 59, wherein the processor is programmed to provide a signal indicative of a low flow condition upon receiving the threshold signal from only one of the sensors.

71. A device according to claim 59, wherein the processor is programmed to provide a signal indicative of a low flow condition upon receiving the threshold signal from only one of the sensors and for less than a predetermined period.

72. A device according to claim 59, wherein the processor is programmed to receive the threshold signals from the sensors when the device is primed.

73. A device according to claim 43, wherein the flow path includes a reservoir containing a therapeutic fluid.

74. A device according to claim 73, wherein the therapeutic fluid is insulin.

75. A device according to claim 73, further comprising a fill port connected to the reservoir.

76. A device according to claim 73, wherein the reservoir is pressurized.

77. A device according to claim 43, wherein the exit port assembly includes a transcutaneous patient access tool.

78. A device according to claim 77, wherein the transcutaneous patient access tool comprises a needle.

79. A device according to claim 43, wherein a combined volume of the exit port assembly and the flow path is fixed and predetermined.

80. A device according to claim 43, wherein possible expansion of a combined volume of the exit port assembly and the flow path is relatively small compared with the volume of the sensor chamber.

81. A device according to claim 43, further comprising:
  a dispenser for causing fluid through the flow path to the exit port assembly;
  a local processor connected to the dispenser and programmed to cause fluid flow to the exit port assembly based upon flow instructions;
  a wireless receiver connected to the local processor for receiving flow instructions from a separate, remote control device and delivering the flow instructions to the local processor; and
  a housing containing the flow path, the exit port assembly, the dispenser, the local processor, and the wireless receiver, wherein the housing is free of user input components for providing flow instructions to the local processor.

82. A system including a fluid delivery device according to claim 81, and further comprising a remote control device separate from the fluid delivery device and including:
  a remote processor;
  user interface components connected to the remote processor for allowing a user to provide flow instructions to the remote processor; and
  a transmitter connected to the remote processor for transmitting the flow instructions to the receiver of the fluid delivery device.

83. A device according to claim 43, further comprising:
  a dispenser for causing fluid through the flow path to the exit port assembly;
  a local processor connected to the dispenser and programmed to cause fluid flow to the exit port assembly based upon flow instructions, and further programmed to provide flow information;
  a wireless transmitter connected to the local processor for transmitting the flow information from the local processor to a separate, remote control device; and
  a housing containing the flow path, the exit port assembly, the dispenser, the local processor, and the wireless transmitter, wherein the housing is free of user output components for providing the flow information from the local processor to a user.

84. A system including a fluid delivery device according to claim 83 and further comprising a remote control device separate from the fluid delivery device and including:
  a remote processor;
  user output components connected to the remote processor for allowing a user to receive flow information; and
  a receiver connected to the remote processor for receiving the flow information from the transmitter of the fluid delivery device.

85. A system according to claim 83, wherein the remote control device includes an alarm connected to the remote processor.

86. A device according to claim 43, wherein the sensors each comprise:
  a first electrode secured on the diaphragm;
  a second electrode positioned in a fixed location with respect to the first electrode; and
  an impedance meter connected between the first and the second electrodes.

* * * * *